US012465521B2

(12) United States Patent
Hallen

(10) Patent No.: US 12,465,521 B2
(45) Date of Patent: Nov. 11, 2025

(54) HYBRID 2-PORT VITRECTOMY AND COMBINED TREATMENT AND INFUSION PROBE

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 337 days.

(21) Appl. No.: 18/303,105

(22) Filed: Apr. 19, 2023

(65) Prior Publication Data

US 2023/0346600 A1 Nov. 2, 2023

Related U.S. Application Data

(60) Provisional application No. 63/363,739, filed on Apr. 28, 2022.

(51) Int. Cl.
*A61F 9/008* (2006.01)

(52) U.S. Cl.
CPC .... *A61F 9/008* (2013.01); *A61F 2009/00874* (2013.01)

(58) Field of Classification Search
CPC .. A61F 9/008; A61F 9/00821; A61F 9/00825; A61F 9/00763; A61F 2009/00874
USPC .......................................................... 606/4–6
See application file for complete search history.

(56) References Cited

U.S. PATENT DOCUMENTS

| | | | |
|---|---|---|---|
| 4,011,869 A | 3/1977 | Seiler, Jr. | |
| 5,651,783 A | 7/1997 | Raynard | |
| 9,956,053 B2 | 5/2018 | Diao et al. | |
| 10,376,414 B2 | 8/2019 | Hallen et al. | |
| 2005/0245916 A1* | 11/2005 | Connor | A61B 90/30 606/4 |
| 2008/0172078 A1* | 7/2008 | Svetic | A61B 17/320783 606/171 |
| 2010/0106054 A1* | 4/2010 | Hangai | A61F 9/00821 600/566 |
| 2013/0090635 A1* | 4/2013 | Mansour | A61F 9/00821 606/4 |
| 2017/0165114 A1* | 6/2017 | Hallen | A61F 9/00736 |
| 2017/0172796 A1 | 6/2017 | Biancalana et al. | |
| 2021/0290438 A1 | 9/2021 | Hallen | |

* cited by examiner

*Primary Examiner* — Nathan J Jenness

(57) ABSTRACT

The present disclosure generally relates to microsurgical instruments for ophthalmic surgical procedures, and more particularly, methods and microsurgical instruments for vitreoretinal procedures. In certain embodiments described herein, a vitreoretinal procedure is performed utilizing two surgical instruments: 1) a treatment instrument configured to a) treat a target ophthalmic tissue (e.g., sever and remove the vitreous body), and b) infuse fluid into the intraocular space to maintain intraocular pressure (IOP); and 2) an illumination probe for providing illumination within the intraocular space. The combined treatment and infusion functionalities of the treatment instrument eliminate the need for a separate infusion cannula, thus enabling the vitreoretinal procedure to be performed with only two instruments and reducing the number of incisions made in the eye. Additionally, utilization of two instruments facilitates easier manipulation of the eye by a surgeon, as one of the two instruments can be used to "steer" the eye during the procedure.

11 Claims, 12 Drawing Sheets

HYBRID 2-PORT VITRECTOMY AND COMBINED TREATMENT AND INFUSION PROBE

BACKGROUND

Anatomically, the human eye is divided into two distinct regions—the anterior segment and the posterior segment. The anterior segment includes the lens and extends from the outermost layer of the cornea to the posterior of the lens capsule. The posterior segment of the eye includes the anterior hyaloid membrane and all of the ocular structures behind it, such as the vitreous humor, retina, choroid, and the optic nerve.

Vitreoretinal procedures are commonly performed within the posterior segment of the human eye to treat serious conditions such as age-related macular degeneration (AMD), macular holes, premacular fibrosis, retinal detachment, epiretinal membrane, cytomegalovirus (CMV) retinitis, diabetic retinopathy, vitreous hemorrhages, and other ophthalmic conditions. Such procedures frequently require the severance and removal of portions of the vitreous humor (i.e., the "vitreous") from the posterior segment of the eye, which is a colorless and gel-like substance that makes up approximately two-thirds of the eye's volume. The procedure for severing and removing the vitreous from the eye is referred to as a "vitrectomy."

In a vitrectomy procedure, a surgeon inserts microsurgical instruments through one or more incisions made in the eye to cut and remove the vitreous from within. A separate incision may be provided for each microsurgical instrument when using multiple instruments simultaneously. The microsurgical instruments typically utilized during a vitrectomy procedure include: a vitrectomy instrument (e.g., treatment instrument) for severing and removing the vitreous body; an illumination probe for providing illumination within the intraocular space; and an infusion cannula for infusing fluid into the intraocular space to maintain intraocular pressure (IOP). In certain cases, to reach the vitreous located at peripheral regions of the eye, surgeons may also utilize a scleral depressor to displace the retina inward, in addition to other microsurgical instruments. Thus, during any given vitrectomy procedure, or any vitreoretinal procedure for that matter, three or more microsurgical instruments may be simultaneously used, whereas the surgeon only has two hands to perform the procedure.

SUMMARY

The present disclosure generally relates to methods and microsurgical instruments for ophthalmic surgical procedures, and more particularly, methods and microsurgical instruments for vitreoretinal procedures.

In certain embodiments, a surgical instrument for performing an ophthalmic surgical procedure is provided. The surgical instrument includes a handpiece and a probe disposed through an opening in a distal end of the handpiece and configured to be inserted into an intraocular space of an eye. The probe further includes an infusion portion having a first diameter, and a treatment portion distal to the infusion portion and having a second diameter smaller than the first diameter. The infusion portion includes a port for directing fluid into a surgical site within the intraocular space and a channel fluidly coupled to the port for delivering the fluid to the port. The treatment portion includes a device for treating a tissue at a surgical site.

In certain embodiments, a system for performing an ophthalmic surgical procedure is provided. The system includes an endoillumination instrument and a treatment instrument for treating a tissue in an intraocular space of an eye. The treatment instrument includes a handpiece and a probe disposed through an opening in a distal end of the handpiece. The probe is configured to be inserted into the intraocular space of the eye, and includes an infusion portion having a first diameter and a treatment portion distal to the infusion portion and having a second diameter smaller than the first diameter. The infusion portion includes a port for directing fluid into a surgical site within the intraocular space and a channel fluidly coupled to the port for delivering the fluid to the port. The treatment portion includes a device for treating a tissue at a surgical site. At least one of the endoillumination instrument and the treatment instrument are configured to be manipulated by a surgeon to control a position of an eye during the ophthalmic surgical procedure.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to methods and microsurgical instruments for ophthalmic surgical procedures, and more particularly, methods and microsurgical instruments for vitreoretinal procedures. In certain embodiments described herein, a vitreoretinal procedure is performed utilizing two surgical instruments: 1) a treatment instrument configured to a) treat a target ophthalmic tissue (e.g., sever and remove the vitreous body), and b) infuse fluid into the intraocular space to maintain intraocular pressure (IOP); and 2) an illumination probe for providing illumination within the intraocular space. The combined treatment and infusion functionalities of the treatment instrument eliminate the need to utilize a separate infusion cannula, thus enabling the vitreoretinal procedure to be performed with only two instruments and reducing the number of incisions made in the eye. Additionally, the utilization of two instruments facilitates easier manipulation of the eye by a surgeon, as one of the two instruments can be used to "steer" the eye during the procedure. Thus, the methods and instruments described herein enable not only improved safety during vitreoretinal procedures, but also improved procedural efficiency and control as compared to utilizing three or more instruments, or a single instrument.

Figure 1:
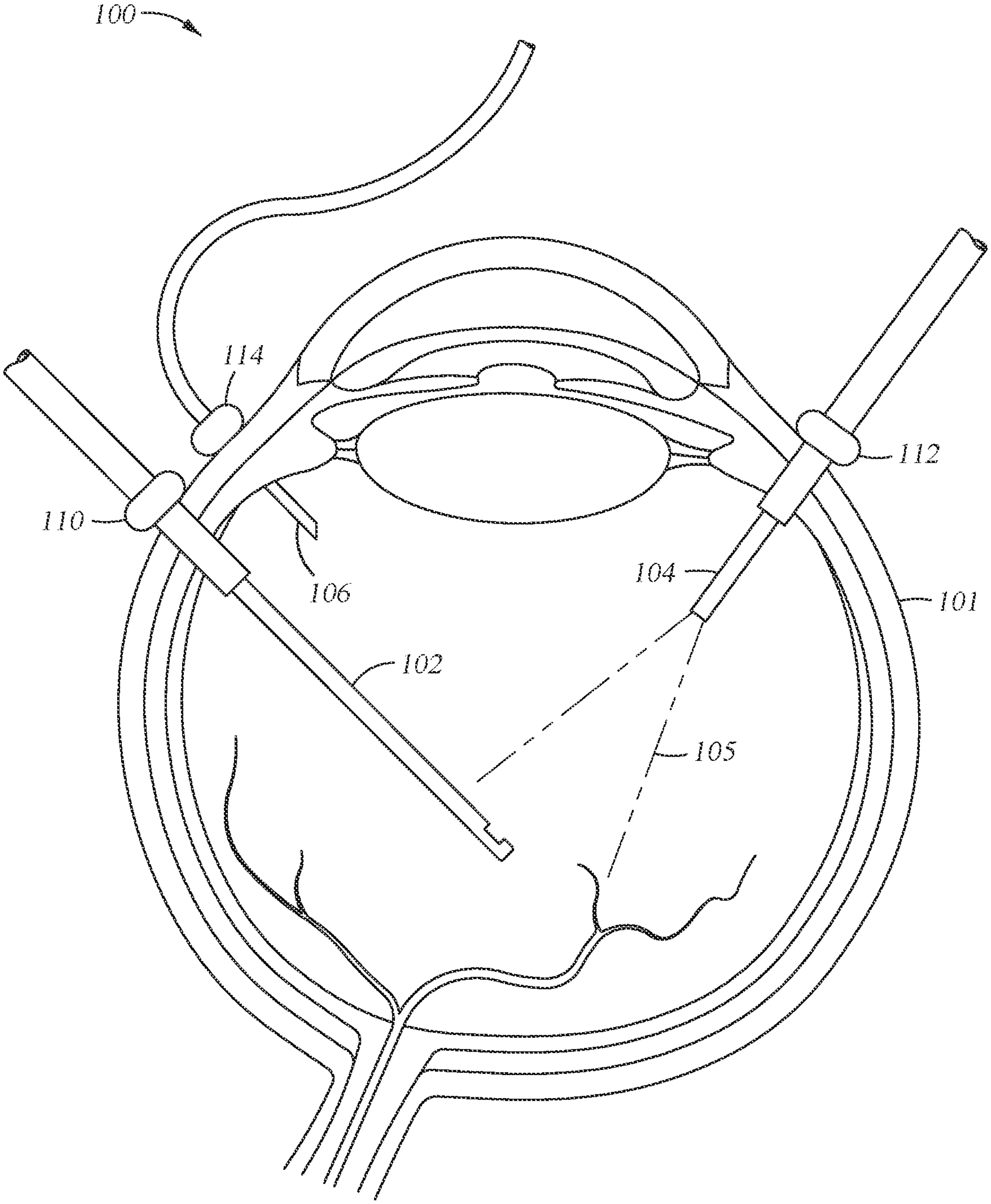
FIG. 1 illustrates various conventional surgical instruments utilized with current methods of performing vitreoretinal procedures, in accordance with certain embodiments of the present disclosure.

FIG. 1 illustrates various conventional surgical instruments utilized with current methods for performing vitreoretinal procedures. In particular, FIG. 1 schematically depicts a cross-sectional side view of eye 100 undergoing a vitreoretinal surgical procedure, with three instruments inserted therein: a treatment instrument 102, here being a vitrectomy instrument for cutting and removing the eye's vitreous gel in a slow, controlled fashion; a light pipe 104, which provides illumination 105 inside eye 100, referred to as endoillumination; and an infusion cannula 106, used to replace fluid in the eye with a saline solution and to maintain proper intraocular pressure (IOP). Treatment instrument 102, infusion cannula 104, and light pipe 106 are typically used in combination and are inserted into eye 100 through respective trocar cannulas 110, 112 and 114 that are inserted into separate incisions in sclera 101, as would be understood by skilled persons. Accordingly, three distinct incisions must be made for a single vitreoretinal procedure. Even further, because three instruments are inserted into eye 100 at once, the operating space within eye 100 may be limited.

Figure 2:
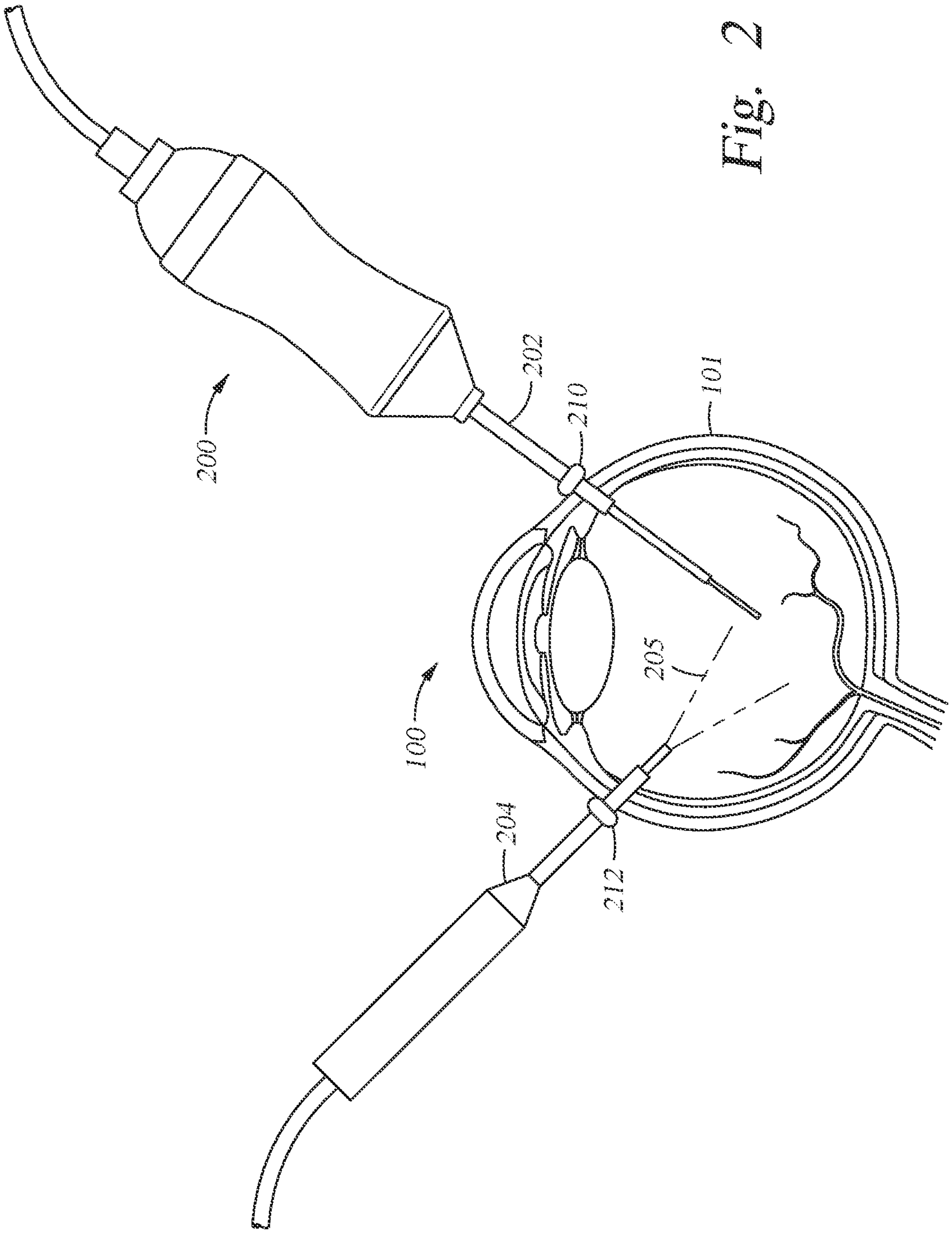
FIG. 2 illustrates improved surgical instruments facilitating improved methods for performing vitreoretinal procedures, in accordance with certain embodiments of the present disclosure.

FIG. 2 illustrates improved surgical instruments facilitating improved methods for performing vitreoretinal procedures, in accordance with certain embodiments of the present disclosure. More particularly, FIG. 2 schematically depicts a cross-sectional side view of eye 100 undergoing a vitreoretinal surgical procedure, e.g., a vitrectomy, with two instruments inserted therein, instead of three: treatment instrument 200, which provides the combined functions of treatment (here, cutting and removal of the eye's vitreous, i.e., vitrectomy) and infusion (replacing fluid in the eye to maintain IOP); and, light pipe 204, which provides endoillumination 205 inside eye 100. The two instruments, 200 and 204, may together be referred to as a "system." By utilizing treatment instrument 200 with combined vitrectomy and infusion functionality, the need to utilize a separate infusion cannula, such as infusion cannula 106 in FIG. 1, is eliminated. Thus, only two incisions in sclera 101 are needed for performing a vitreoretinal procedure (e.g., to insert treatment instrument 200 and light pipe 204 into eye 100 via two respective trocar cannulas 210 and 212), thereby improving the overall safety of the procedure. Additionally, the utilization of two instruments facilitates easy manipulation of eye 100 by a surgeon, as one of treatment instrument 200 and light pipe 204 can be used to "steer" the eye during the procedure.

Figure 3:
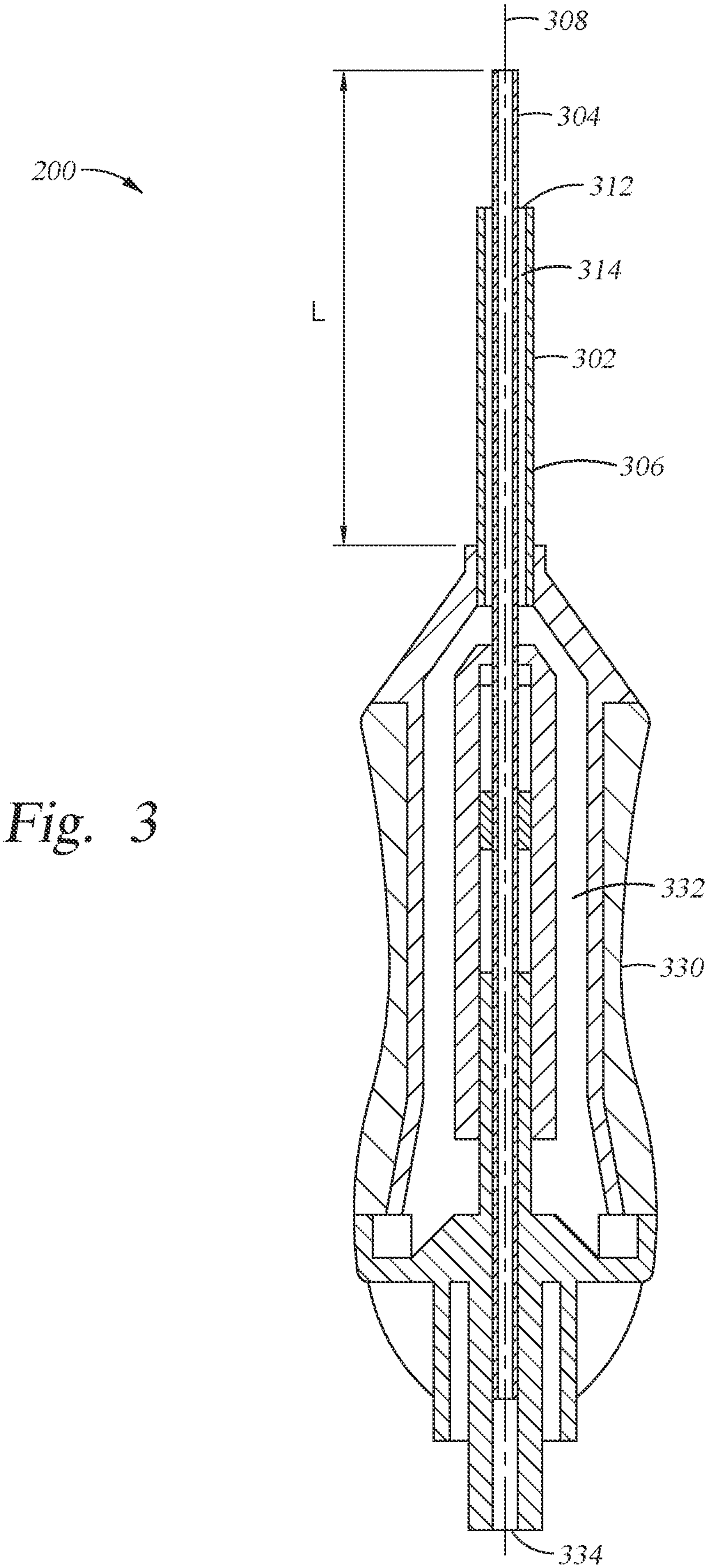
FIG. 3 illustrates an enlarged cross-sectional side view of a surgical instrument in FIG. 2, in accordance with certain embodiments of the present disclosure.

FIG. 3 illustrates an enlarged cross-sectional side view of treatment instrument 200 in FIG. 2, in accordance with certain embodiments of the present disclosure. As shown, treatment instrument 200 comprises probe 302 and handpiece 330. Probe 302 further comprises treatment portion 304 and infusion portion 306, which are coaxially aligned along a central axis 308. Probe 302 is a hybrid gauge system because it includes an exterior surface having different cross-section widths. For example, in the example shown, probe 302 steps down in diameter, or cross-section, from infusion portion 306 to treatment portion 304. Such an arrangement may be referred to as a "stepped" or "telescoping" profile.

Treatment portion 304 comprises a device that performs the treatment function of treatment instrument 200. For example, in embodiments where treatment instrument 200 comprises a vitrectomy instrument (i.e., a vitrector), treatment portion 304 performs a vitrectomy function, e.g., detaching vitreous from the retina and aspirating the vitreous from the eye. In such embodiments, treatment portion 304, and thus, treatment instrument 200, may comprise a mechanical vitrectomy device (e.g., a cutter), further described with reference to FIG. 4. In certain other such embodiments, treatment portion 304, and thus, treatment instrument 200, may comprise a laser vitrectomy device, further described with reference to FIG. 5A-5I. As shown, treatment portion 304 extends distally from a distal end of handpiece 330, and may be directly or indirectly attached thereto within lumen 332 of handpiece 330.

Infusion portion 306 is arranged as an outermost surface of probe 302 and is disposed adjacent to treatment portion 304 such that at least a portion of treatment portion 304 is surrounded by infusion portion 306. Similar to treatment portion 304, infusion portion 306 extends distally from the distal end of handpiece 330, and may be directly or indirectly attached thereto within interior lumen 332. Infusion portion acts to direct infusion fluid into the surgical region. As shown, infusion portion 306 comprises one or more infusion ports 312 that direct infusion fluid into the surgical region. Generally, infusion fluid may be directed distally and coaxially with probe 302 by infusion portion 306. In certain embodiments, infusion portion 306 forms channel 314 leading to and fluidly coupled with infusion ports 312. In certain embodiments, channel 314 is a single, annular channel formed between infusion portion 306 and treatment portion 304. In other embodiments, a plurality of channels 314 are formed in infusion portion 306 and spaced about treatment portion 304. For example, a specific embodiment includes two channels 314 spaced about 180 degrees apart. In another specific embodiment, three channels 314 are spaced about 120 degrees apart. In certain embodiments, channel(s) 314 are formed as grooves in the inner surface of infusion portion 306. Fluid provided from, e.g., a fluid source may be fed to treatment instrument 200 and then to channel(s) 314 and out of infusion ports 312.

In the hybrid gauge probe 302 shown, infusion portion 306 has a larger diameter than treatment portion 304. It therefore has a larger cross-sectional distance than treatment portion 304. While the diameter of infusion portion 306 may be any suitable size, in certain embodiments, the diameter is selected to be within a range of about 15-30 gauge, and may, in certain examples, be selected to be within a range of about 18-27 gauge. Similarly, in certain embodiments, the diameter of treatment portion 304 is selected to be within a range of about 15-30 gauge, and may, in certain examples, be selected to be within a range of about 18-27 gauge. In specific embodiments, the diameter of infusion portion 306 is about 23 gauge, and the diameter of treatment portion 304 is about 25 gauge. In other specific embodiments, the diameter of infusion portion 306 is about 25 gauge, and the diameter of treatment portion 304 is about 27 gauge. In still other specific embodiments, the diameter of infusion portion 306 is about 27 gauge, and the diameter of treatment portion 304 is about 29 gauge. While described in terms of diameter, some embodiments have non-circular (non-cylindrical) outer surfaces, and therefore the cross-sectional distance may be used in place of diameter. For example, some probes/instruments may have a cross-section comprising an oval, quadrilateral, polygonal, or other shape.

Generally, infusion portion 306, which has a larger diameter than treatment portion 304, may span a longer distance along length L or probe 302 as compared to treatment portion 304 to provide optimal stiffness for treatment instrument 200, thereby improving ease of use and safety. In certain embodiments, treatment portion 304 spans a distance of between about 55% and about 95% of length L, such as a distance of between about 60% and about 90% of length L, such as a distance of about 75% of length L.

Generally, handpiece 330 has an outer surface configured to be held by a user, such as a surgeon. For example, handpiece 330 may be ergonomically contoured to substantially fit the hand of the user. In certain embodiments, the outer surface may be textured or have one or more gripping features formed thereon, such as one or more grooves and/or ridges. Handpiece 330 may be made from any materials commonly used for such instruments and suitable for ophthalmic surgery. For example, handpiece 330 may be formed of a lightweight aluminum, a polymer, or other suitable material. In some embodiments, handpiece 330 may be sterilized and used in more than one surgical procedure, or may be a single-use device. Handpiece 330 further includes one or more ports 334 at a proximal end thereof for providing ingress/egress for supply lines (e.g., a fluid supply line, vacuum supply line, power supply line, etc.) from various sources to be routed into lumen 332 of handpiece 3300. For example, port 334 may provide a fluid connection between handpiece 330 and a fluid supply line further coupled to a fluid source for infusion. In another example, port 334 may provide an optical connection between handpiece 330 and an optical fiber cable that couples to one or more light sources for providing laser light and/or illumination light. In certain embodiments, such sources are disposed in, or in communication with, a surgical console. The surgical console may include multiple functions, subassemblies, equipment, and other capabilities for performing one or more surgical procedures, including vitreoretinal procedures.

Figure 4:
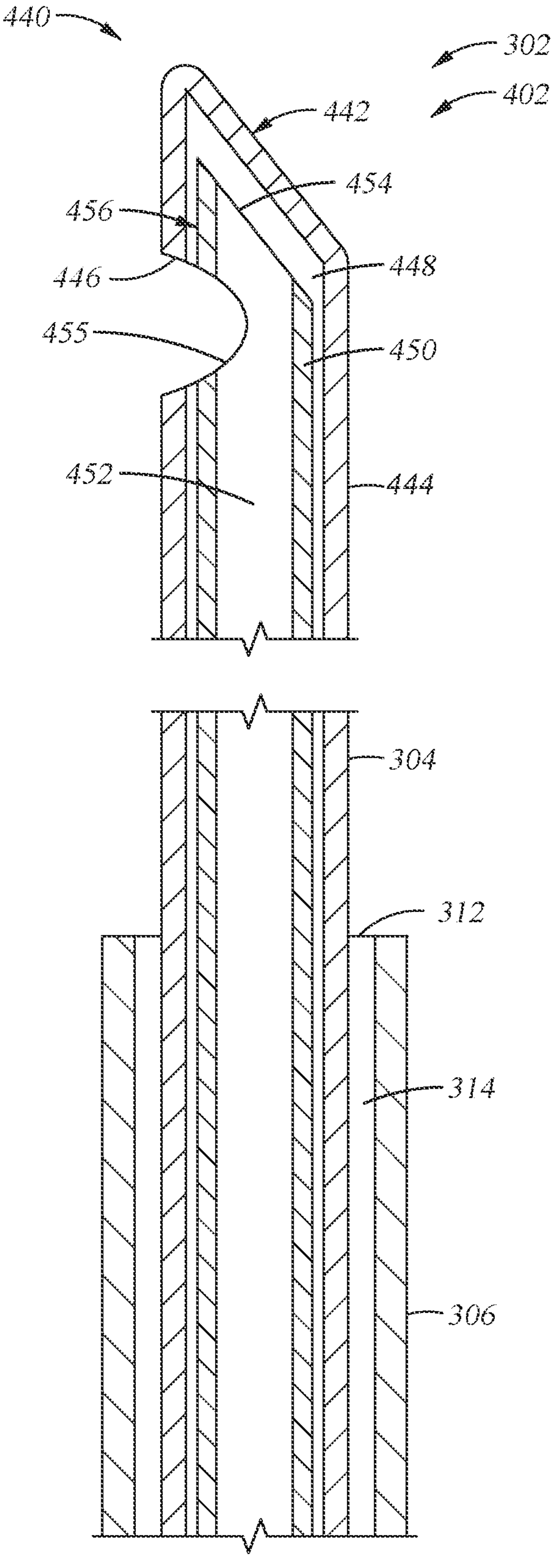
FIG. 4 illustrates a cross-sectional side view of a portion of the surgical instrument of FIG. 3, in accordance with certain embodiments of the present disclosure.

FIG. 4 illustrates a cross-sectional side view of one embodiment of probe 302 of treatment instrument 200 in FIG. 3, in accordance with certain embodiments of the present disclosure. More particularly, FIG. 4 illustrates an embodiment where probe 302 comprises mechanical vitrectomy probe 402, and thus, treatment portion 304 comprises a mechanical vitrectomy device. In such embodiments, treatment portion 304 may be coupled to an actuator 404 disposed in handpiece 330, such as a pneumatic actuator. In specific examples, the pneumatic actuator may include a reciprocating air driven diaphragm.

As shown, treatment portion 304, which extends distally from handpiece 330, includes outer tube 444. Generally, outer tube 444 may be formed of conventional surgical-grade materials, such as aluminum, stainless steel (e.g., 316 or 316L stainless steel), or other alloys. In particular examples, outer tube 444 is formed of Phynox, Elgiloy, or other suitable cobalt-chromium-nickel alloys, or nitinol or other suitable nickel-titanium alloys. Outer tube 444 comprises a closed end face 442 at distal end 440, which, in certain embodiments, may be beveled (e.g., disposed at a non-normal angle relative to a major axis of mechanical vitrectomy probe 402). Note that in other embodiments, end face 442 may be disposed at an angle normal to the major axis of mechanical vitrectomy probe 402. Outer tube 444 further comprises outer port 446, which is configured to receive tissue, such as ophthalmic tissue, for severing and aspirating. Outer port 446 is in fluid communication with inner channel 448 of outer tube 444, which further comprises inner tube 450 disposed therein. Inner tube 450 includes inner bore 452, open end 454, and cutting surface 456. In certain embodiments, inner tube 450 may further comprise inner port 455. Generally, inner bore 452 is in fluid communication with an aspiration line that connects to a vacuum pressure for pulling tissue into outer port 446 when inner tube 450 is located away from outer port 446. Inner tube 450 moves within inner channel 448 of outer tube 444 to cut tissue that is pulled into outer port 446 by the aspiration system. The ophthalmic tissue received by outer port 446 may include vitreous or ocular membranes.

When used to cut tissue, inner tube 450 may be initially moved away from outer port 446 and the vacuum pressure pulls tissue into outer port 446 and inner channel 448. Inner tube 450 then moves toward outer port 446 and severs the tissue within inner channel 448. The severed tissue is pulled through inner bore 452 of inner tube 450 by the aspiration system. In certain embodiments, severed tissue is pulled through inner port 455 of inner tube 450. Inner tube 450 then moves away from outer port 446, and the cutting process is repeated. A cutting cycle may include moving inner tube 450 to open outer port 446 and then moving inner tube 450 to close outer port 446 to initiate the cut, and then returning inner tube 450 to its starting position for the next cutting cycle.

Mechanical vitrectomy probe 402 further comprises infusion portion 306, as described in FIG. 3. Infusion portion 306 acts to direct infusion fluid into the surgical region, and may be utilized sequentially or simultaneously with treatment portion 304. As shown, infusion portion 306 comprises one or more infusion ports 312 that distally direct infusion fluid into the surgical region coaxially with a major axis of probe 402. In certain embodiments, infusion portion 306 forms channel 314 leading to infusion ports 312, which may be a single, annular channel formed between infusion portion 306 and treatment portion 304. In other embodiments, a plurality of coaxial channels 314 are formed in infusion portion 306 and spaced about treatment portion 304. Fluid provided from, e.g., a fluid source may be fed to treatment instrument 200 and then to channel(s) 314 and out of infusion ports 312. By having both treatment portion 304 and infusion portion 306, mechanical vitrectomy probe 402 provides the dual functionalities of mechanical vitrectomy and infusion, and thus, eliminates the need to utilize a separate infusion cannula during a vitreoretinal procedure.

Figure 5A:
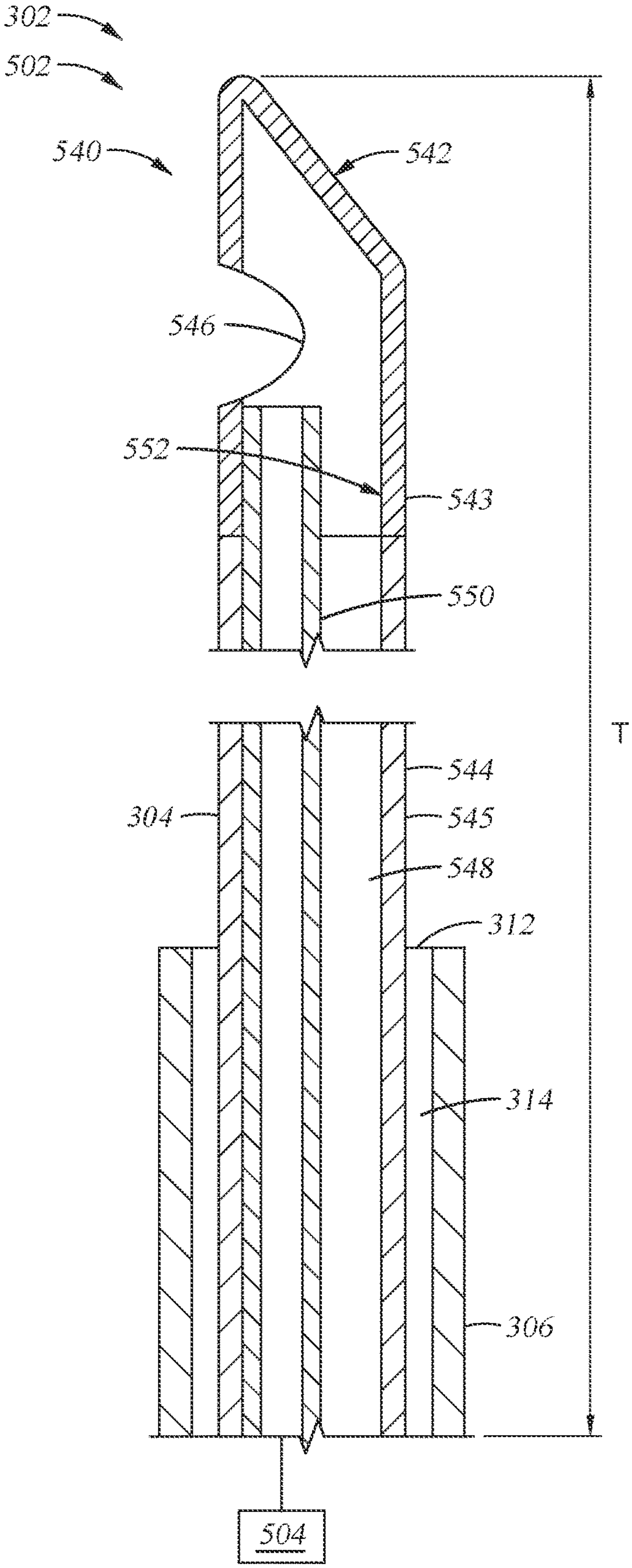
FIG. 5A illustrates a cross-sectional side view of a portion of the surgical instrument of FIG. 3, in accordance with certain embodiments of the present disclosure.

FIG. 5A illustrates a cross-sectional side view of another exemplary embodiment of probe 302 of treatment instrument 200 in FIG. 3, in accordance with certain embodiments of the present disclosure. More particularly, FIG. 5A illustrates an embodiment where probe 302 comprises a laser vitrectomy probe 502 and thus, treatment portion comprises a laser vitrectomy device. In such embodiments, treatment portion 304 comprises an elongated laser cutting member, which may be aspirating (e.g., having a port for aspiration of ophthalmic tissue) or non-aspirating (e.g., having no port for aspiration of ophthalmic tissue).

As shown, treatment portion 304, which extends distally from handpiece 330, includes tube 544. In certain embodiments, tube 544 may have one or more portions formed of a translucent or transparent material, such as a plastic and/or polymeric material, and one or more other portions formed of more conventional surgical-grade materials, such as aluminum, stainless steel (e.g., 316 or 316L stainless steel), or other alloys. In certain embodiments, one or more portions of tube 544 may be formed of Phynox, Eligiloy, or nitinol. In the example of FIG. 5A, proximal portion 545 of tube 544, which may comprise about 75% or more of a total length T of tube 544, is formed of a metallic material, such as aluminum, stainless steel, Phynox, Eligiloy, or nitinol, while distal portion 543, which may comprise 25% or less of a total length T of tube 544, is formed of a translucent or transparent plastic or polymeric material.

Tube 544 comprises a closed end face 542 at distal end 540 of laser vitrectomy probe 502, which, in certain embodiments, may be beveled (e.g., disposed at a non-normal angle relative to a major axis of laser vitrectomy probe 502). Note that in other embodiments, end face 542 may be disposed at an angle normal to a major axis of laser vitrectomy probe 502. In FIG. 5A, which depicts an aspirating example of laser vitrectomy probe 502, tube 544 further comprises port 546 in distal portion 543, which is configured to receive tissue, such as ophthalmic tissue. Port 546 is in fluid communication with inner channel 548, which is at least partially defined by inner sidewall 552 of tube 544 and comprises optical fiber 550 disposed therein. In the example of FIG. 5A, optical fiber 550 extends along inner sidewall 552 of tube 544 and terminates adjacent to port 546. In some other examples, optical fiber 550 may terminate within port 546 (e.g., terminate between distal and proximal ends of port 546). In some other examples, optical fiber 550 may be spaced away (e.g., separated) from inner sidewall 552, and may, in certain examples, be centrally disposed within channel 548. Optical fiber 550 is configured to propagate and emit laser light for severing ophthalmic tissue received through port 546 and, in certain embodiments, is further configured to propagate and emit illumination light for illuminating a surgical site. In certain embodiments, inner channel 548 is in fluid communication with an aspiration line that connects to a vacuum pressure for pulling ophthalmic tissue into port 546. Accordingly, when (e.g., as soon as) ophthalmic tissue is drawn into tube 544, e.g., through port 546, the ophthalmic tissue passes through a volume irradiated by laser light emitted by optical fiber 550, thus severing the ophthalmic tissue. The severed ophthalmic tissue is then aspirated proximally through inner channel 548 of tube 544, which provides a coaxial path for aspiration of severed ophthalmic tissues through laser vitrectomy probe 502.

Note that in non-aspirating examples, tube 544 may not comprise port 546, and optical fiber 550 may terminate adjacent to end face 542, which may beveled.

The laser light and/or illumination light propagated and emitted by optical fiber 550 may be produced by one or more light sources 504 optically coupled to optical fiber 550. Such light sources 504 may be disposed in, e.g., a surgical console, with which laser vitrectomy probe 502 is coupled to via an optical fiber cable. In certain embodiments, the laser light produced by light source(s) 504 and propagated by optical fiber 550 is an ultraviolet ("UV") (<350 nanometers (nm)) laser light. In other embodiments, the laser light is an argon blue-green laser light (488 nm), a Nd-YAG laser light (532 nm) such as a frequency-doubled Nd-YAG laser light, a krypton red laser light (647 nm), a diode laser light (805-810 nm), or any other suitable type of laser light for ophthalmic surgery. In certain embodiments, light source(s) 504 may produce a laser light that has a pulse rate within a range of about 10 kilohertz (kHz) and about 500 kHz. This range can effectively provide disruption of ophthalmic tissues, such as the vitreous. "Disruption" refers to the breaking down of tissue by rapid ionization of molecules thereof. Other pulse rate ranges can also provide disruption and are thus contemplated as well. In some examples, light source(s) 504 may produce a picosecond or femtosecond laser light. In some embodiments, light source(s) 504 may produce a continuous coherent laser light. For example, light source(s) 504 may produce a continuous coherent laser light at low power.

In embodiments where light source(s) 504 produce illumination light, the illumination light may include UV light, violet light, blue light, white light, infrared ("IR") light, or any other suitable type of illumination light. In certain embodiments, light source(s) 504 include an LED-based (light-emitting diode based) illumination light source, a xenon-based illumination light source, or a halogen-based illumination light source. In certain embodiments, propagation of illumination light 562 through optical fiber 550 and into an intraocular space may be modulated by utilizing different types of illumination light sources, utilizing different materials for optical fiber 550, modifying the physical arrangement of optical fiber 550 within the laser vitrectomy probe 502, and/or by utilizing different materials for the probe.

In certain embodiments, optical fiber 550 is communicatively coupled to a digital visualization system, such as the NGENUITY® 3D Visualization System produced by Alcon. Other digital visualization systems, including those produced by other manufacturers, are also contemplated for use with the embodiments described herein. Utilization of a digital visualization system may enable modification of the color and intensity of, e.g., illumination light 562 emitted from optical fiber 550 by adjustment of hue, saturation, gamma, tint, and/or other light parameters.

While "light" is discussed herein, the scope of the disclosure is not intended to be limited to visible light. Rather, other types of radiation, such as UV and IR radiation, may be transmitted from optical fiber 550, and the term "light" is intended to encompass all types of radiation for use with optical fiber 550. In some examples, non-visible light may be transmitted by optical fiber 550 and captured by non-visible light sensors for analysis with the digital visualization systems described above. Thus, a non-visible light source may be coupled to optical fiber 550 in addition to an illumination light source and/or a laser light source, and the non-visible light may be propagated simultaneously with or sequentially pulsed with laser light 560 and illumination light 562.

Figure 5B:
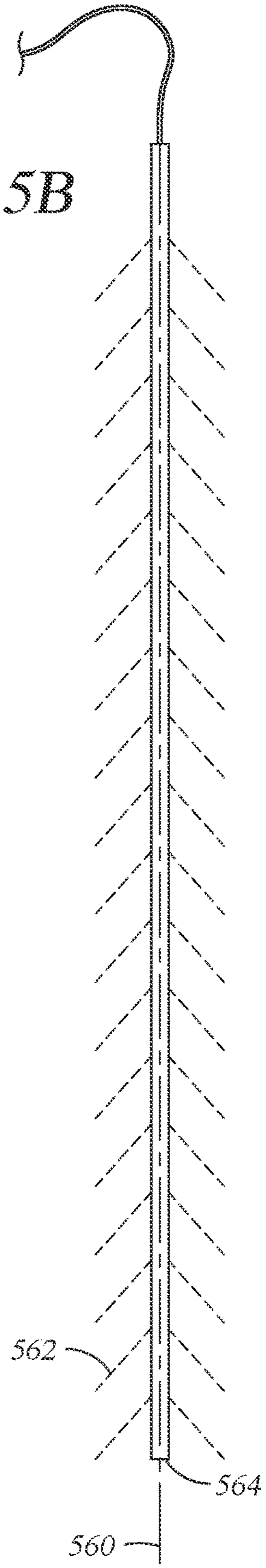
FIG. 5B illustrates a longitudinal schematic view of a portion of the surgical instrument in FIG. 5A, in accordance with certain embodiments of the present disclosure.
Figure 5C:
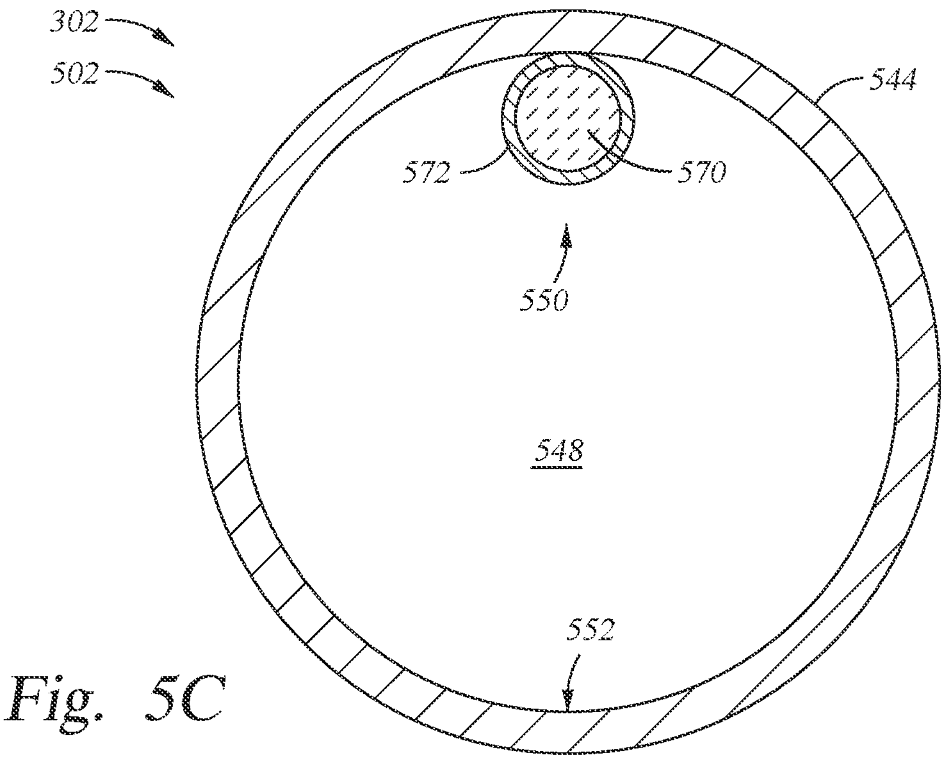
FIG. 5C illustrates a front sectional view of the surgical instrument in FIG. 5A, in accordance with certain embodiments of the present disclosure.
Figure 5D:
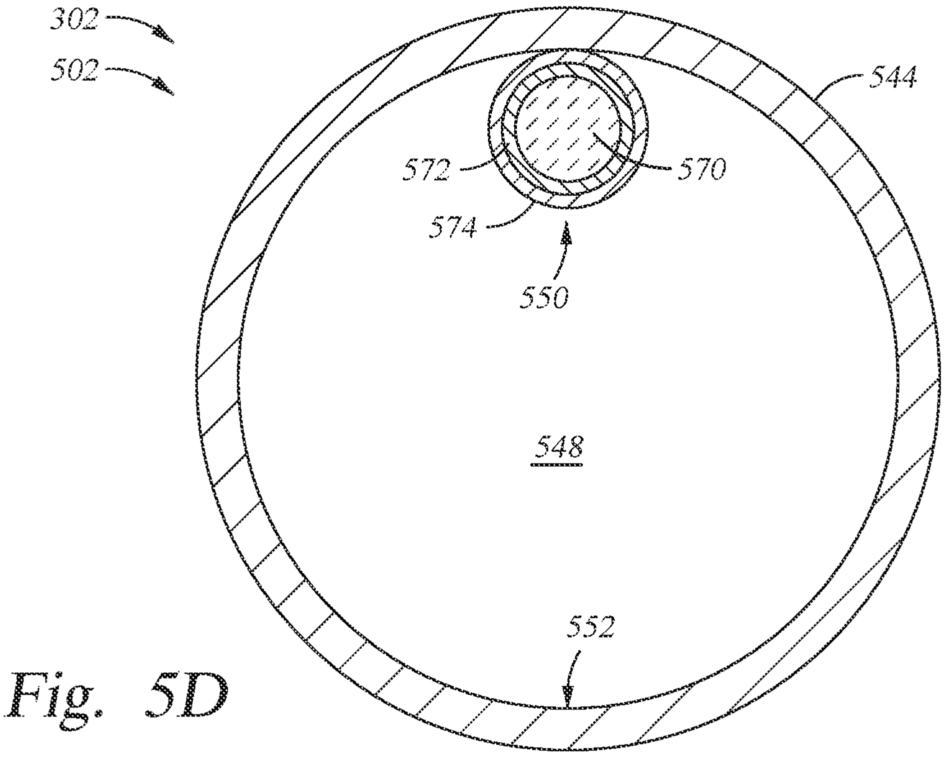
FIG. 5D illustrates a front sectional view of the surgical instrument in FIG. 5A, in accordance with certain embodiments of the present disclosure.
Figure 5E:
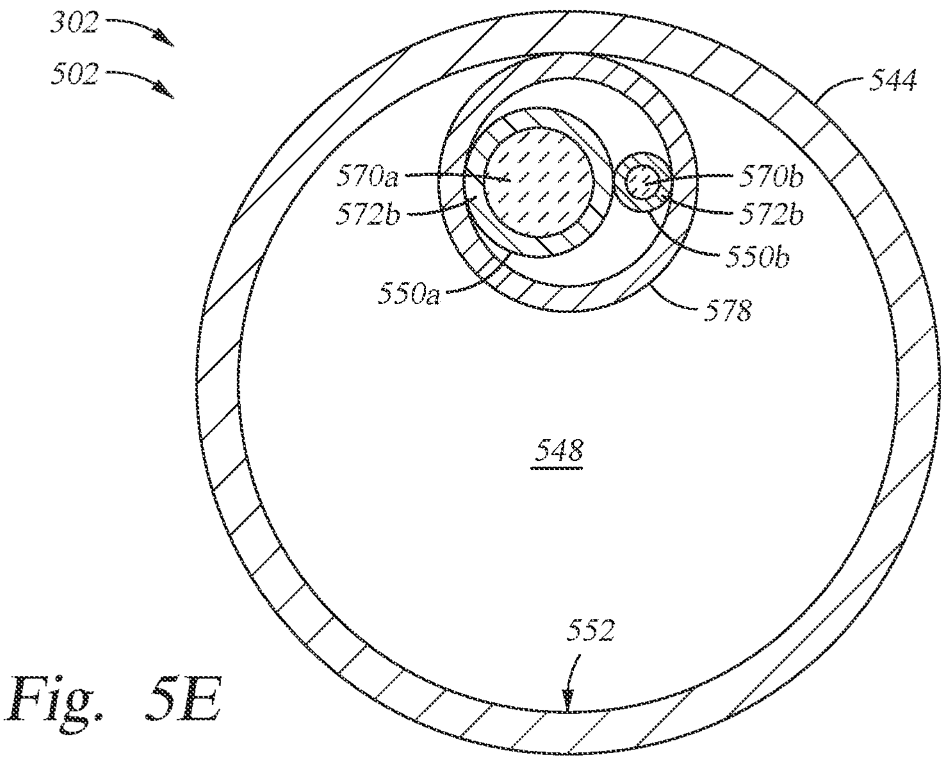
FIG. 5E illustrates a front sectional view of the surgical instrument in FIG. 5A, in accordance with certain embodiments of the present disclosure.
Figure 5F:
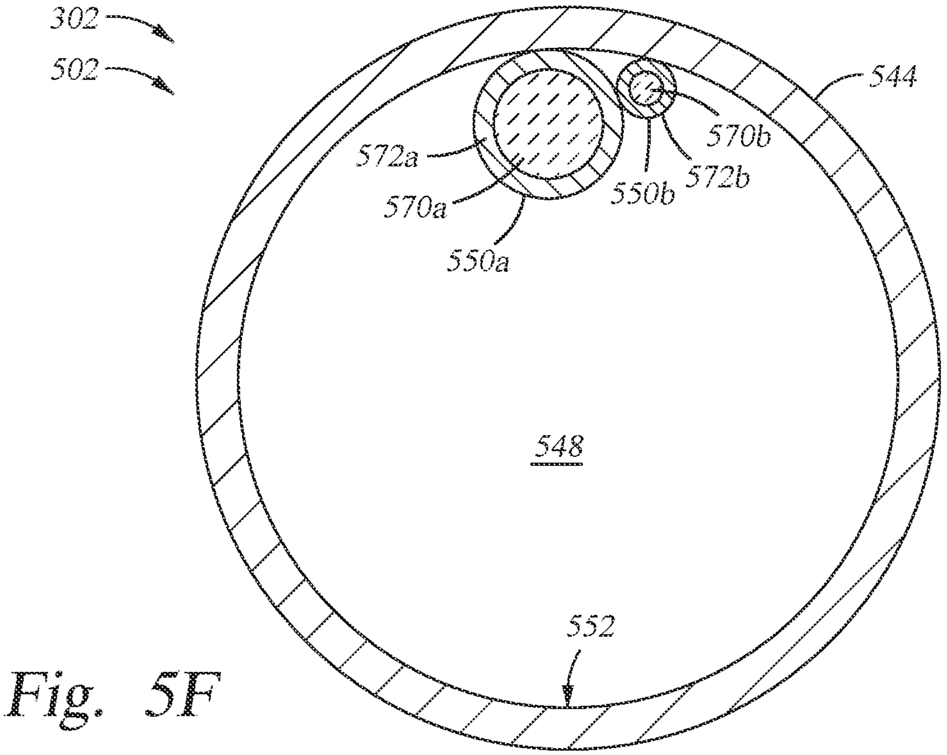
FIG. 5F illustrates a front sectional view of the surgical instrument in FIG. 5A, in accordance with certain embodiments of the present disclosure.
Figure 5G:
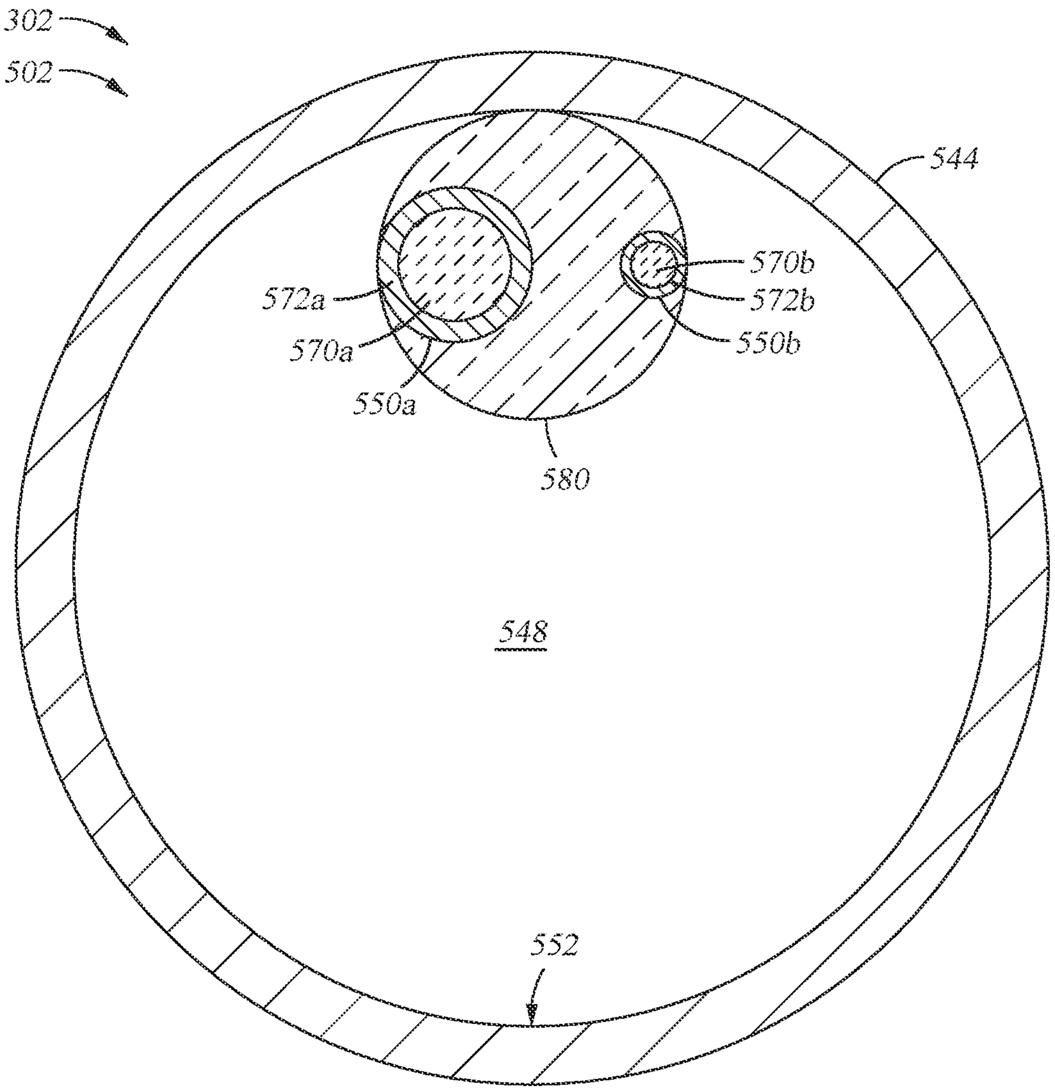
FIG. 5G illustrates a front sectional view of the surgical instrument in FIG. 5A, in accordance with certain embodiments of the present disclosure.

As described above, optical fiber 550 is configured to project laser light and, in certain examples, illumination light. Utilization of a laser vitrectomy probe configured to project both laser light (for tissue severance) and illumination light may be beneficial since the projected illumination light may provide enhanced visualization of the intraocular space during severance and removal of the ophthalmic tissues, particularly when utilized in combination with a light pipe, e.g., light pipe 204. In certain examples, a single optical fiber 550, e.g., as shown in FIG. 5A, may be used for projecting both laser light and illumination light. Examples of using a single optical fiber configured to project both laser light and illumination light are depicted in FIGS. 5B-5D. In other embodiments, however, two or more optical fibers may be used within a laser vitrectomy probe; for example, one or more optical fibers may be configured to project laser light, while one or more additional optical fibers may be configured to project illumination light. Various examples of using multiple fibers for projecting laser light and illumination light are depicted in FIGS. 5E-5G.

Laser vitrectomy probe 502 further comprises infusion portion 306, as described in FIGS. 3 and 4. Again, infusion portion 306 acts to direct infusion fluid into the surgical region, and may be utilized sequentially or simultaneously with treatment portion 304. By having both treatment portion 304 and infusion portion 306, laser vitrectomy probe 502 provides the dual functionalities of laser vitrectomy and infusion, and thus, eliminates the need to utilize a separate infusion cannula during a vitreoretinal procedure.

FIG. 5B illustrates an example of a single optical fiber 550 propagating both laser light 560 and illumination light 562 therefrom. In the example of FIG. 5B, laser light 560 is emitted through terminal end 564 of optical fiber 550, while illumination light 562 is emitted radially outward from optical fiber 550, in addition to or alternatively from being emitted through terminal end 564. Accordingly, optical fiber 550 in FIG. 5B may be considered an edge-emitting or side-emitting fiber, wherein illumination light 562 is not completely reflected within optical fiber 550, and is therefore emitted through a sidewall of a cladding thereof. In certain other embodiments, however, optical fiber 550 may be an end-emitting fiber, wherein illumination light 562 (and laser light 560) undergoes total internal reflection within optical fiber 550, and therefore, is only projected from terminal end 564. Wherein illumination light 562 is emitted through terminal end 564, illumination light 562 may be coaxially projected with laser light 560, or may be diffusely projected from terminal end 564. Generally, illumination light 562 may be propagated simultaneously with laser light 560, or may be sequentially pulsed with laser light 560.

To achieve the propagation depicted in FIG. 5B, laser light 560 may be focused by light source(s) 504 onto a core of optical fiber 550 to transmit laser light 560 through the core, while illumination light 562 may be focused by light source(s) 504 onto a cladding of optical fiber 550 to transmit illumination light 562 through the cladding. In certain other embodiments, however, illumination light 562 may be focused onto both the cladding and the core of optical fiber 550, in which case both the cladding and the core transmit illumination light 562. In still other embodiments, illumination light 562 may be focused onto only the core of optical fiber 550, thereby being transmitted only through the core. Thus, optical fiber 550, including a core and a cladding, may be capable of transmitting laser light 560 (through the core) and illumination light 562 (through the cladding and/or the core) in the same fiber. In certain embodiments, illumination light 562 is propagated through one or more additional cores in optical fiber 550. Thus, optical fiber 550 may include one or more cores through which laser light 560 and illumination light 560 are separately propagated.

FIGS. 5C and 5D illustrate exemplary front sectional views of treatment portion 304 of laser vitrectomy probe 502 in FIG. 5A having a single optical fiber 550 housed therein for projecting both laser and illumination lights. As depicted, treatment portion 304 has a circular cross section defined by tube 544. Generally, optical fiber 550 includes core 570 and cladding 572 circumferentially surrounding core 570, in accordance with embodiments of the present disclosure. Core 570 may comprise any transparent material, such as fused silica or glass. In some embodiments, core 570 is doped. For example, core 570 may be germanium-doped silica. Doping the core 570 with germanium or a similar dopant may increase the refractive index of core 570 compared to that of cladding 572 material, hence enabling laser and light guiding properties within core 570.

Cladding 572 may also comprise a transparent material, such as fused silica or glass. In some embodiments, cladding 572 is doped in addition to or instead of doping core 570. For example, cladding 572, which may comprise fused silica, is doped with a dopant that reduces the refractive index of cladding 572 relative to that of core 570. Example dopants include fluorine (F), chlorine (Cl), boron (B), or the like. Cladding 572, when doped, has a lower refractive index than core 570, thus enabling light guiding properties within core 570. Although one cladding 572 is depicted in each of FIGS. 5C and 5D, optical fiber 550 may further include one or more additional claddings.

In certain embodiments, as depicted in FIG. 5D, optical fiber 550 is disposed within sleeve 574. Sleeve 574 may couple directly or indirectly to an exterior of cladding 572 and circumferentially surround cladding 572 and core 570 of optical fiber 550 therewithin. Sleeve 574 may act as a tubular structure for providing structural support and alignment of optical fiber 550 within channel 548 of tube 544. Similar to core 570 and cladding 572, sleeve 574 may comprise a transparent material such as fused silica and glass. In further embodiments, sleeve 574 is doped with a dopant to manipulate the refractive index of sleeve 574 as desired.

FIGS. 5C and 5D illustrate exemplary arrangements wherein optical fiber 550 is disposed against inner sidewall 552 of tube 544. Note that, in other embodiments, however, optical fiber 550 may be suspended within channel 548, and thus may not be in contact with inner sidewall 552 of tube 544. In the examples of FIGS. 5C and 5D, optical fiber 550 may be coupled to the inner sidewall 552 along a longitudinal portion thereof radially aligned with port 546 (shown in FIG. 5A). Thus, space 576 is formed within channel 548 around optical fiber 550 but for the longitudinal portion of inner sidewall 552 to which optical fiber 550 is attached.

Such an arrangement may enable improved aspiration of severed ophthalmic tissue through the interior of the laser vitrectomy probe 502. Optical fiber 550 may be coupled or bonded to inner sidewall 552 via any suitable adhesive or bonding mechanism. For example, an exterior surface of cladding 572 or sleeve 574 may be bonded to inner sidewall 552 with an epoxy or acrylic adhesive, though other adhesives are also contemplated.

FIGS. 5E-5G illustrate exemplary front sectional views of treatment portion 304 of laser vitrectomy probe 502 in FIG. 5A having at least two optical fibers 550*a*, 550*b* housed therein. In such examples, a first optical fiber 550*a* may be utilized to propagate laser light for tissue severance and a second optical fiber 550*b* may be utilized to propagate illumination light for illumination of a surgical site. Each of optical fibers 550*a*, 550*b* further includes core 570*a*, 570*b* and cladding 572*a*, 572*b*, respectively. Cores 570*a*, 570*b* and claddings 572*a*, 572*b* may be formed of any suitable materials for propagation of laser and illumination light beams, respectively. For example, cores 570*a*, 570*b* and claddings 572*a*, 572*b* may comprise a transparent material such as fused silica or glass, as described above. Cores 570*a*, 570*b* and claddings 572*a*, 572*b* may further be doped with one or more dopants depending on desired refractive properties for each of optical fibers 550*a*, 550*b*.

Note that although depicted as having different dimensions in FIGS. 5E-5G, optical fibers 550*a*, 550*b* and cores 570*a*, 570*b* and claddings 572*a*, 572*b* may have similar or different dimensions to each other.

In FIG. 5E, optical fibers 550*a*, 550*b* are both disposed within inner tube 578, which is itself is disposed in channel 548. Similar to sleeve 574, tube 578 may provide structural support and containment of optical fibers 550*a*, 550*b* within channel 548 of laser vitrectomy probe 502. Inner tube 578 may comprise a transparent material such as fused silica and glass. In further embodiments, inner tube 578 is doped with a dopant to manipulate the refractive index of inner tube 578 as desired. In some embodiments, a transparent filler material may be used within the inner tube 578 to prevent movement of optical fibers 550*a*, 550*b* within. For example, an adhesive may fill all areas within the inner tube 578 that are not occupied by optical fibers 550*a*, 550*b*. In other embodiments, optical fibers 550*a*, 550*b* are disposed within inner tube 578 without the utilization of a filler material.

FIGS. 5F and 5G illustrate alternative exemplary arrangements of optical fibers 550*a*, 550*b* without the utilization of inner tube 578. In FIG. 5F, optical fibers 550*a*, 550*b* are disposed within channel 548 of tube 544 without any surrounding structure other than tube 544 itself. In some examples, optical fibers 550*a*, 550*b* may be coupled together within channel 548, such as by bonding with an adhesive. In other embodiments, optical fibers 550*a*, 550*b* may be separate and isolated from each other within channel 548. In FIG. 5G, optical fibers 550*a*, 550*b* are placed through spacer tube 580 having one or more longitudinal bores 582 drilled therethrough to allow placement of optical fibers 550*a*, 550*b*. Spacer tube 580 may act in a substantially similar manner to inner tube 578 and provide structural support and containment of optical fibers 550*a*, 550*b*. Spacer tube 580 may be formed of any suitable transparent materials, including fused silica and/or glass.

Regardless of whether the optical fibers 550*a*, 550*b* are contained within another structure in channel 548, optical fibers 550*a*, 550*b* may be arranged to either directly or indirectly contact inner sidewall 552 or be suspended without any contact with inner sidewall 552. FIGS. 5E-5G illustrate examples where 550*a*, 550*b* are either directly or indirectly coupled to the inner sidewall 552. As described above, the optical fibers 550*a*, 550*b* may be directly or indirectly coupled to the inner sidewall 552 via any suitable adhesive or bonding mechanism, such as an epoxy or acrylic adhesive. Note that that although only two optical fibers 550*a*, 550*b* are illustrated in FIGS. 5E-5G, more than two optical fibers may be utilized in substantially similar arrangements.

Figure 5H:
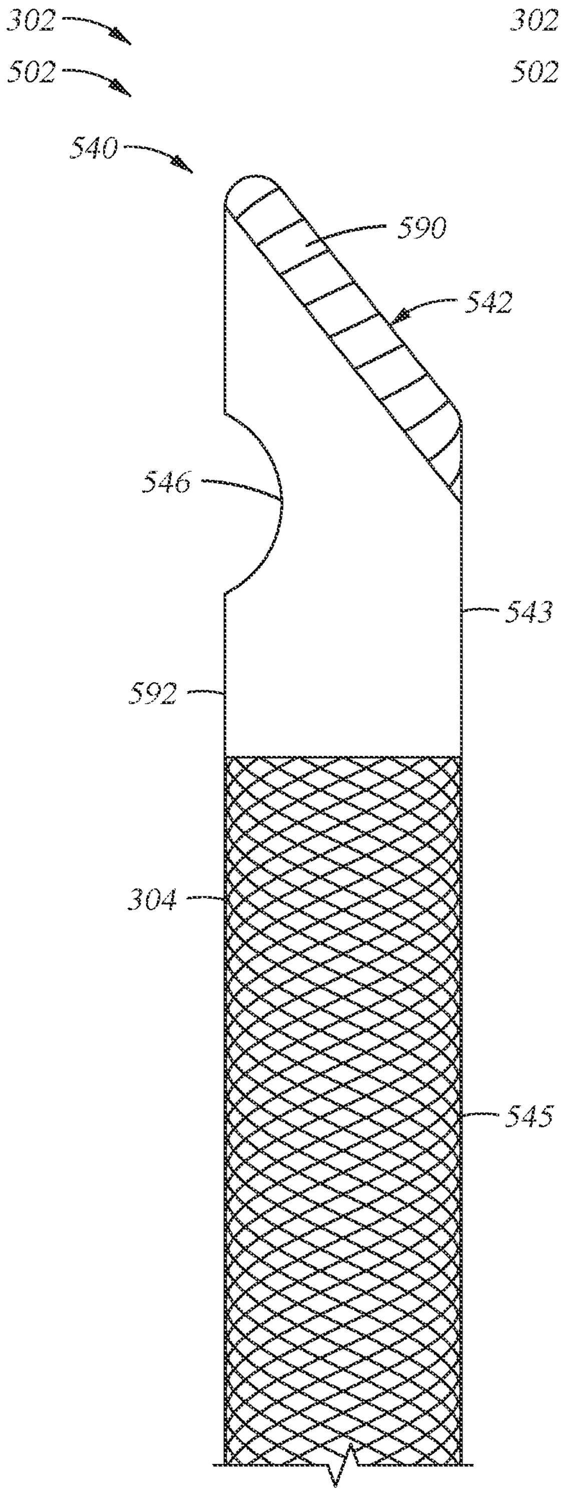
FIG. 5H illustrates a plan view of a portion of the surgical instrument in FIG. 5A, in accordance with certain embodiments of the present disclosure.
Figure 5I:
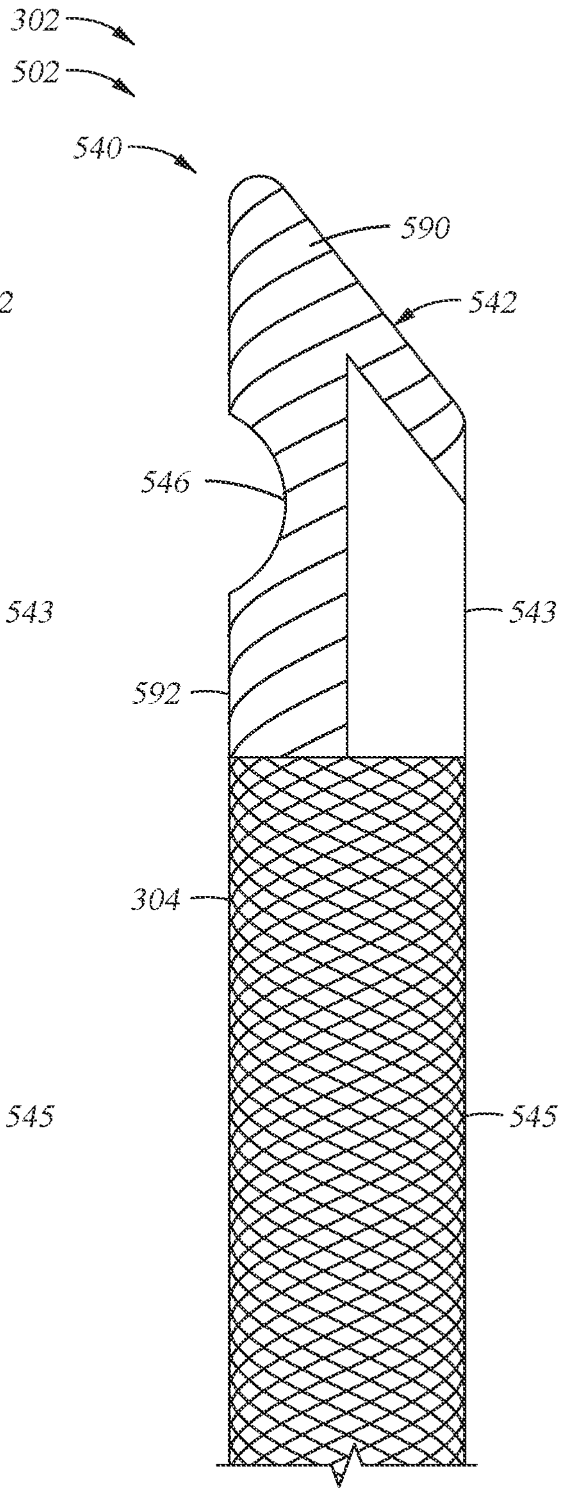
FIG. 5I illustrates a plan view of a portion of the surgical instrument in FIG. 5A, in accordance with certain embodiments of the present disclosure.

FIGS. 5H and 5I illustrate plan views of treatment portion 304 of laser vitrectomy probe 502 in FIG. 5A having different exemplary arrangements of masking 590 to modify the propagation of illumination light through distal portion 543, which may otherwise be formed of a translucent or transparent material. Masking 590 refers to any suitable device, material, or mechanism for reducing or preventing transmission of illumination light therethrough. For example, masking 590 may refer to areas of laser vitrectomy probe 502 having a higher refractive index relative to other areas of the probe. In some examples, masking 590 refers to opaque or semi-opaque portions laser vitrectomy probe 502 through which reduced or no illumination light may pass. In still other examples, masking 590 refers to an opaque or semi-opaque film or layer applied to an exterior or interior surface of laser vitrectomy prove 502. In any form, masking 590 may be disposed on distal portion 543 of tube 544 in any suitable arrangement to provide optimal illumination of a surgical site, while also reducing phototoxic effects on surrounding tissues and reducing glare for a user of laser vitrectomy probe 502.

In one exemplary embodiment depicted in FIG. 5H, distal portion 543 of tube 544 is substantially transparent but for end face 542, which partially or entirely comprises masking 590. During vitrectomy, distal end 540 of laser vitrectomy probe 502 is often placed in close proximity to the retina of a patient's eye, and excess illumination propagated through end face 542 may cause retinal damage. Thus, utilization of the masking arrangement in FIG. 5H is particularly beneficial for reducing or eliminating retinal damage caused by illumination light being transmitted axially through end face 542, while still allowing illumination light to be transmitted radially outward, in substantially 360°, from distal portion 543.

FIG. 5I depicts another exemplary embodiment substantially similar to that of FIG. 5H, where masking 590 is disposed on end face 542 and further extends proximally along portside 592 of distal portion 543 to form a mask around port 546. Thus, masking 590 may extend from end face 542 to at least a proximal end of port 546. The additional masking around port 546 may further reduce glare caused by illumination light being transmitted through the sidewalls of tube 544 in the direction of the tissues to be severed/aspirated, thereby improving visibility for the user during a vitreoretinal procedure. In certain embodiments, masking 590 forms a perimeter around (e.g., surround) port 546, and port 546 may be described as being "fenced in" by masking 590. In certain embodiments, as shown in FIG. 5I, masking 590 may extend proximally beyond port 546, such as up to proximal portion 545 of tube 544. Herein, "portside" refers to an arc, or portion of the circumference, of tube 544 comprising port 546. In certain embodiments, masking 590 is formed on a portion of portside 591 having an angular measurement between about 20° and about 120°, or between about 20° and 90°, or between about 20° and 45°, out of 360°.

Although many of the embodiments described above are generally directed to instruments for vitrectomies, the concepts exemplified therewith may be applied to instruments for other types of ophthalmic procedures. For example, other types of vitreoretinal procedures may be performed utilizing a treatment instrument with combined treatment and infusion functionalities, in addition to a light pipe or other endoillumination device. FIGS. 6A-6C and FIG. 7 illustrate such exemplary instruments having combined treatment and infusion functionalities, described in more detail below.

Figure 6A:
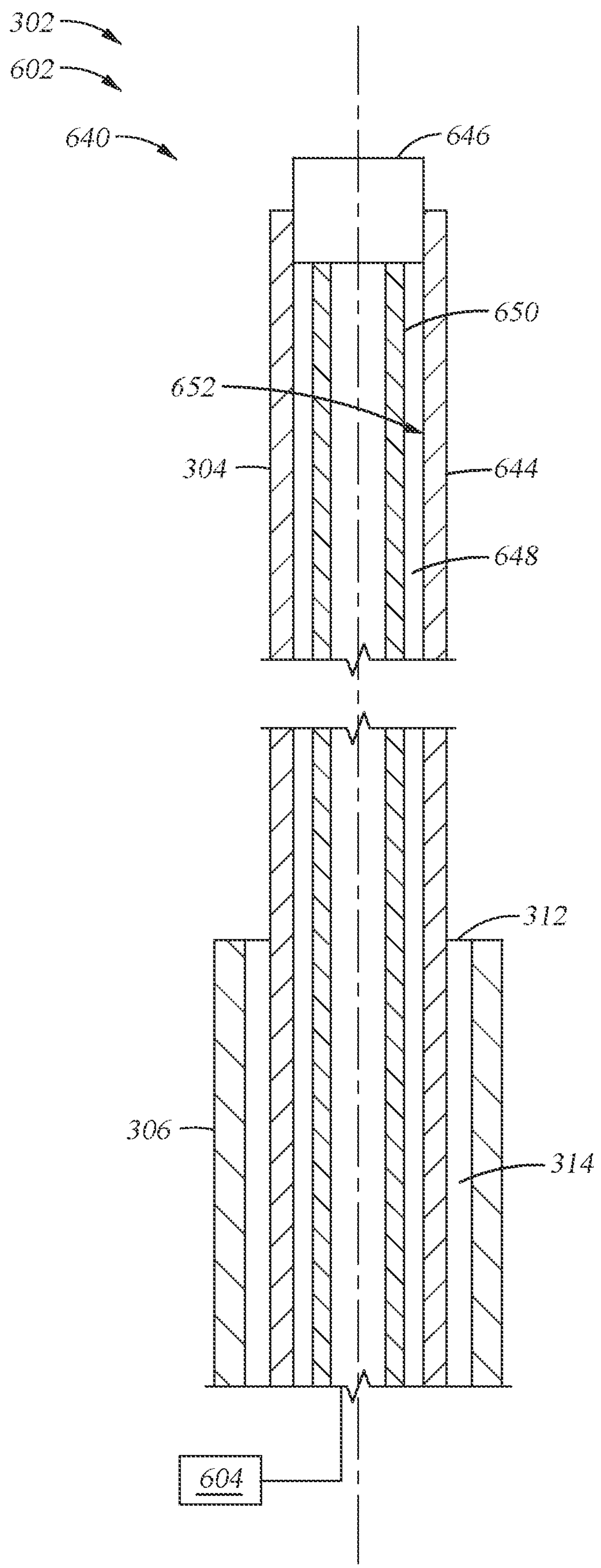
FIG. 6A illustrates a cross-sectional side view of a portion of another exemplary surgical instrument, in accordance with certain embodiments of the present disclosure.

FIG. 6A illustrates a cross-sectional side view of an exemplary embodiment wherein probe 302 of treatment instrument 200 in FIG. 3 comprises laser probe 602, in accordance with certain embodiments of the present disclosure. In such embodiments, treatment portion 304 comprises an elongated laser propagating member, which may be non-aspirating and configured to perform various types of laser-based treatments. In certain embodiments, laser probe 602 is configured to perform laser ablation for performing, e.g., vitrectomy or glaucoma surgical procedures, such as goniotomy, trabeculotomy, and trabeculectomy, as well as other associated procedures. In certain other embodiments, laser probe 602 is configured to perform endophotocoagulation for performing, e.g., retinal repair and reattachment procedures, as well as other associated procedures.

As shown, treatment portion 304, which extends distally from handpiece 330, includes tube 644. In certain embodiments, tube 644 is formed of conventional surgical-grade materials, such as stainless steel and/or aluminum. In certain embodiments, tube 644 may have one or more sections formed of a translucent or transparent material, such as a plastic and/or polymeric material. Window 646 is press fit into tube 644 at distal end 640 of laser probe 602, and, as shown in FIG. 6A, may extend distally therefrom. In certain other embodiments, however, window 646 is flush with the distal end of tube 644. Window 646 comprises an optically clear or transparent material, such as sapphire, fused silica, or other glass or ceramic materials with high transition temperatures. In certain aspects, the transparent material has optical power and, in certain other aspects, the transparent material does not have optical power. Optical power (also referred to as dioptric power, refractive power, focusing power, or convergence power) is the degree to which a lens, mirror, or other optical system converges or diverges light. Accordingly, window 646 may itself be a lens, such as a spherical lens having concave or convex surfaces, or a nonspherical lens.

Tube 644 further comprises inner channel 648, which is at least partially defined by inner sidewall 652 of tube 644 and comprises optical fiber 650 disposed therein. Optical fiber 650, which may be substantially similar to optical fiber 550 in structure and material, is designed to operate as an optical waveguide and propagate laser light through a terminal end thereof. The characteristics of the laser light propagated through optical fiber 650 may be, in certain embodiments, such that the laser light may cause disruption of ophthalmic tissues, and/or in certain embodiments, such that the laser light may cause photocoagulation. In further embodiments, optical fiber 650 is also configured to propagate and emit illumination light for illuminating a surgical site. In still further embodiments, tube 644 may comprise two or more optical fibers for projecting laser light and/or illumination light; for example, one or more optical fibers may be configured to project laser light, while one or more additional optical fibers may be configured to project illumination light. Various examples of using single or multiple fibers for projecting laser light and illumination light are described above with reference to FIGS. 5A-5G—principles described in those examples (e.g., number and arrangement of claddings and cores, materials, and focusing of laser and/or illumination light) may be applied here as well.

In certain embodiments, a terminal end of optical fiber 650 is disposed against or terminates adjacent to window 646 such that the laser light projecting from optical fiber 650 will be projected distally through window 646 with sufficient power to sever ophthalmic tissues (e.g., vitreous) disposed distal to window 646, or to photocoagulate tissues (e.g., retinal structures) disposed distal to window 646. In the example of FIG. 6A, optical fiber 650 is also centrally disposed within channel 648 such that a radial distance between inner sidewall 652 and optical fiber 650 is uniform along a circumference of optical fiber 650. Accordingly, optical fiber 650 does not contact inner sidewall 652 of tube 644 in FIG. 6A. However, in certain embodiments, optical fiber 650 may not be centrally disposed within channel 648, and may, in certain examples, extend along and contact inner sidewall 652 of tube 544.

The laser light and/or illumination light propagated and emitted by optical fiber 650 may be produced by one or more light sources 604 optically coupled to optical fiber 650. Such light sources 604 may be disposed in, e.g., a surgical console, with which laser probe 602 is coupled to via an optical fiber cable. In certain embodiments, the laser light produced by light source(s) 604 and propagated by optical fiber 650 is an ultraviolet ("UV") (<350 nm) laser light. In other embodiments, the laser light is an argon blue-green laser light (488 nm), a Nd-YAG green laser light (532 nm) such as a frequency-doubled Nd-YAG laser light, a krypton red laser light (647 nm), a diode laser light (805-810 nm), or any other suitable type of laser light for ophthalmic surgery. In certain embodiments, light source(s) 604 may produce a laser light that has a pulse rate within a range of about 10 kilohertz (kHz) and about 500 kHz. This range can effectively provide disruption of ophthalmic tissues, such as the vitreous. However, other pulse rate ranges can also provide disruption and are thus contemplated as well. In some examples, light source(s) 604 may produce a femtosecond laser light. In some embodiments, light source(s) 604 may produce a continuous coherent laser light. For example, light source(s) 604 may produce a continuous coherent laser light at low power.

In embodiments where optical fiber 650 propagates illumination light, light source(s) 604 optically coupled therewith may generate UV light, violet light, blue light, white light, infrared ("IR") light, or any other suitable type of illumination light. In certain embodiments, light source(s) 604 include an LED-based illumination light source, a xenon-based illumination light source, or a halogen-based illumination light source. In certain embodiments, propagation of illumination light through optical fiber 650 and into an intraocular space may be modulated by utilizing different types of illumination light sources, utilizing different materials for optical fiber 650, modifying the physical arrangement of optical fiber 650 within the laser probe 602, and/or by utilizing different materials for the probe. In some examples, non-visible light may be transmitted by optical fiber 650 and captured by non-visible light sensors for analysis with the digital visualization systems described above. Thus, a non-visible light source may be coupled to optical fiber 650 in addition to an illumination light source and/or a laser light source, and the non-visible light may be propagated simultaneously with or sequentially pulsed with laser light and illumination light.

In certain embodiments, optical fiber 650 is communicatively coupled to a digital visualization system, such as the NGENUITY® 3D Visualization System produced by Alcon.

Other digital visualization systems, including those produced by other manufacturers, are also contemplated for use with the embodiments described herein. Utilization of a digital visualization system may enable modification of the color and intensity of, e.g., illumination light emitted from optical fiber 650 by adjustment of hue, saturation, gamma, tint, and/or other light parameters.

Laser probe 602 further comprises infusion portion 306, as described in FIGS. 3, 4, and 5A. Again, infusion portion 306 acts to direct infusion fluid into the surgical region, and may be utilized sequentially or simultaneously with treatment portion 304. By having both treatment portion 304 and infusion portion 306, laser probe 602 provides the functionalities of laser ablation and/or photocoagulation and infusion, and thus, eliminates the need to utilize a separate infusion cannula during a vitreoretinal procedure.

Figure 6B:
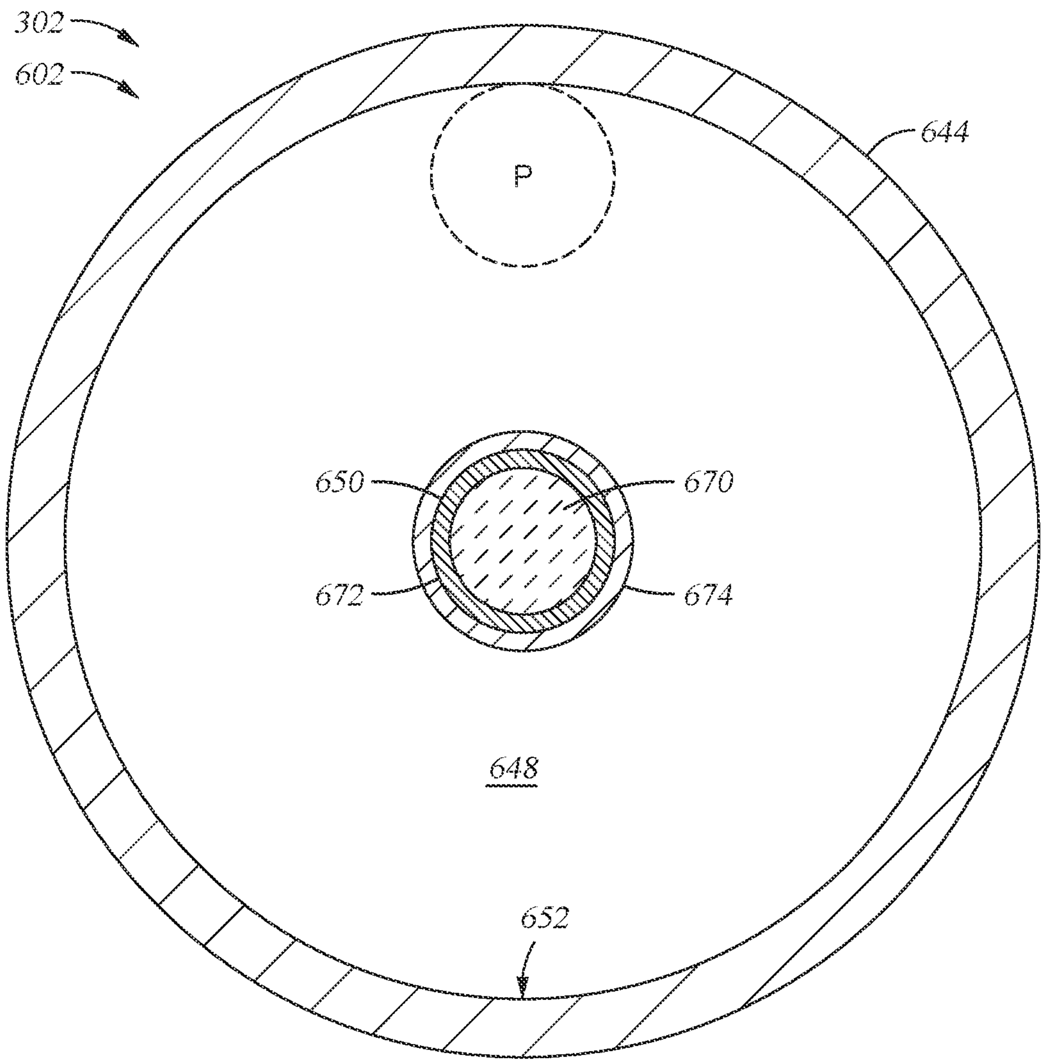
FIG. 6B illustrates a front sectional view of the surgical instrument in FIG. 6A, in accordance with certain embodiments of the present disclosure.

FIG. 6B illustrates an exemplary front sectional view of treatment portion 304 of laser probe 602 of FIG. 6A, having a single optical fiber 650 housed therein for projecting laser light, and, in certain embodiments, illumination light. As depicted, treatment portion 304 has a circular cross-section defined by tube 644. Generally, optical fiber 650 includes core 670 and cladding 672 circumferentially surrounding core 670, in accordance with embodiments of the present disclosure. Core 670 and cladding 672 may generally be formed of the same or similar materials to core 570 and 572 and thus, may function substantially similarly in propagating laser light and/or illumination light. In certain embodiments, as depicted in FIG. 6B, optical fiber 650 is disposed within sleeve 674, which may couple directly or indirectly to an exterior of cladding 672 and circumferentially surround cladding 672. Similar to sleeve 574, sleeve 674 may provide structural support and alignment of optical fiber 650 within channel 648 of tube 644, and may, in certain embodiments, comprise a transparent material such as fused silica and glass. In further embodiments, sleeve 674 is doped with a dopant to manipulate the refractive index of sleeve 674 as desired.

In FIG. 6B, optical fiber 650 is depicted as being centrally disposed within channel 648. However, in certain embodiments, optical fiber may be non-centrally disposed, and may even be disposed against inner sidewall 652 of tube 644, as shown by position P in FIG. 6B. In such embodiments, optical fiber 650 may be coupled or bonded to inner sidewall 652 via any suitable adhesive or bonding mechanism, such as an epoxy or acrylic adhesive. Though only one arrangement of a single optical fiber 650 in laser probe 602 is depicted in FIGS. 6A and 6B, other numbers and/or arrangements of optical fibers are further contemplated, including those described with reference to FIGS. 5A-5G.

Figure 6C:
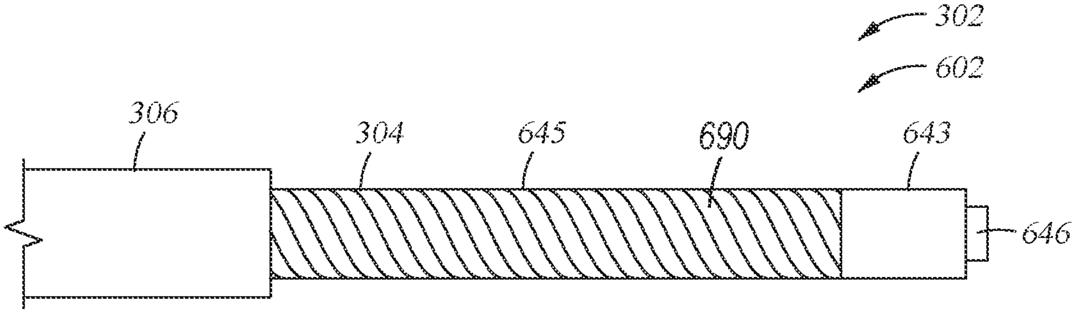
FIG. 6C illustrates a plan view of the surgical instrument in FIG. 6A, in accordance with certain embodiments of the present disclosure.

FIG. 6C illustrates a plan view of treatment portion 304 of laser probe 602 in FIG. 6A having masking 690 formed thereon to modify the propagation of illumination light through distal end 640, which, in certain embodiments, may otherwise be formed of a translucent or transparent material. Like masking 590, masking 690 may refer to any suitable device, material, or mechanism for reducing or preventing transmission of illumination light therethrough. For example, masking 690 may refer to areas of laser probe 602 having a higher refractive index relative to other areas of the probe. In some examples, masking 690 refers to opaque or semi-opaque portions laser probe 602 through which reduced or no illumination light may pass. In still other examples, masking 690 refers to an opaque or semi-opaque film or layer applied to an exterior or interior surface of laser prove 602. In any form, masking 690 may be disposed on tube 644 in any suitable arrangement to provide optimal illumination of a surgical site, while also reducing glare for a user of laser probe 602.

In the exemplary embodiment depicted in FIG. 6C, a majority of tube 644 that is exposed is substantially masked by masking 690, but for small segment at distal end 640, which remains unmasked. More particularly, a proximal portion 645 of tube 644, which comprises about 50% to about 75% of the length ET of an exposed portion of tube 644, comprises masking 690, while a distal portion 643, which comprises about ¼ to about ½ of the length ET, is unmasked. In such embodiments, covering a majority of the exposed portion of tube 644 with masking 690 may significantly reduce glare caused by illumination light being transmitted through the sidewalls of tube 644, thereby improving visibility for a user of a surgical site during a vitreoretinal procedure, which will generally be disposed near distal end 640. However, other arrangements of masking 690 are also contemplated. For example, in certain embodiments, tube 644 may also comprise masking 690 at the distal segment.

Figure 7:
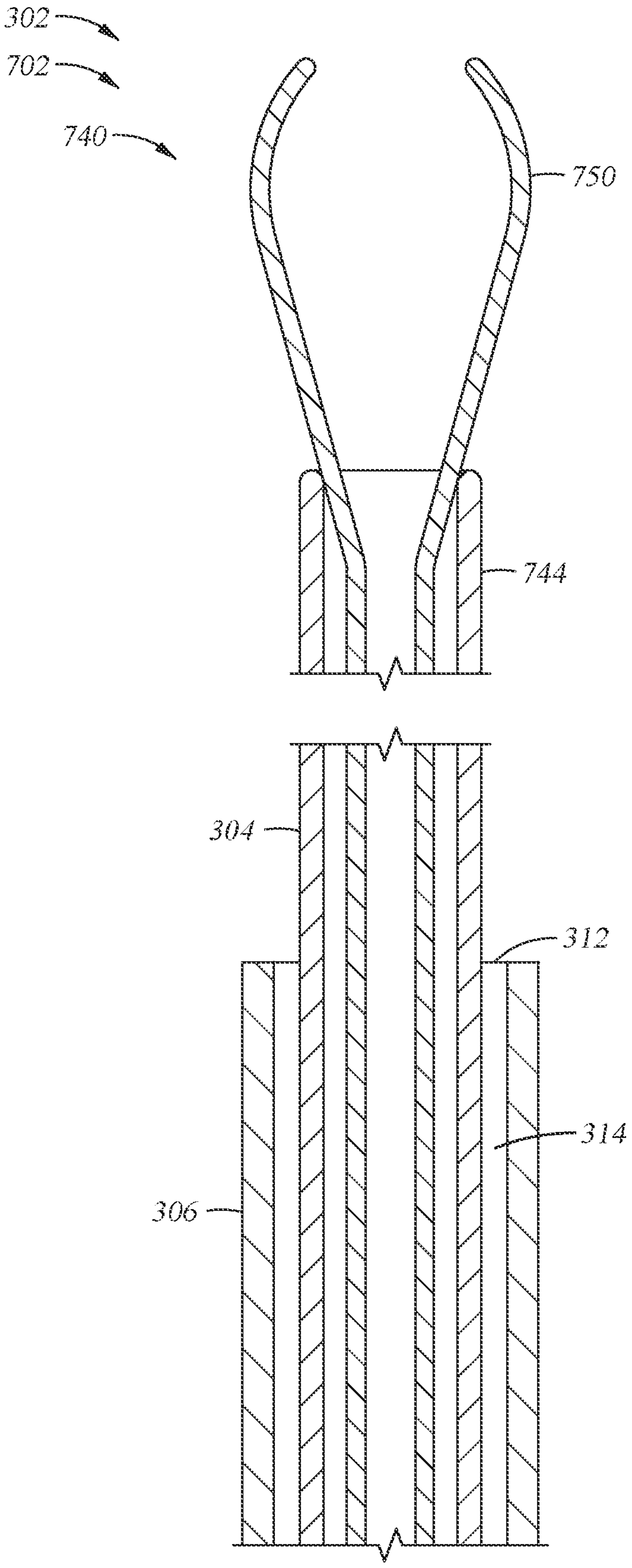
FIG. 7 illustrates a cross-sectional side view of a portion of another exemplary surgical instrument, in accordance with certain embodiments of the present disclosure.

FIG. 7 illustrates a cross-sectional side view of another exemplary embodiment wherein probe 302 of treatment instrument 200 in FIG. 3 comprises mechanical probe 702, in accordance with certain embodiments of the present disclosure. In such embodiments, treatment portion 304 comprises an elongated member 744 having mechanical tool 750 disposed at distal end 740 for mechanically manipulating ophthalmic tissues during a surgical procedure. In the example depicted in FIG. 7, mechanical tool 750 comprises forceps. However, other types of mechanical tools are also contemplated. For example, in certain embodiments, mechanical tool 750 comprises scissors, a blade, a punch, a spatula, a manipulator, or other suitable mechanical tool.

Mechanical probe 702 further comprises infusion portion 306, as described in FIGS. 3, 4, 5A, and 6A. Again, infusion portion 306 acts to direct infusion fluid into the surgical region, and may be utilized sequentially or simultaneously with treatment portion 304. By having both treatment portion 304 and infusion portion 306, mechanical probe 702 provides the dual functionalities of mechanical tissue manipulation and infusion, and thus, eliminates the need to utilize a separate infusion cannula during a vitreoretinal procedure.

In summary, embodiments of the present disclosure include methods, systems, and devices for performing vitreoretinal surgery. In particular, the surgical instruments described above include instruments combining the functions of treatment and intraocular infusion, thus eliminating the need to utilize a separate infusion cannula during a given vitreoretinal procedure. As a result, the vitreoretinal procedure may be performed with only two instruments (e.g., a treatment instrument and a light pipe for illumination), thereby reducing the number of incisions made in the eye. Additionally, the utilization of only two instruments facilitates easier manipulation of the position of the eye during a procedure by a surgeon, as one of the two instruments can be used to “steer” and stabilize the eye during the procedure. Accordingly, the methods and instruments described herein enable not only improved safety during vitreoretinal procedures, but also improved procedural efficiency and control as compared to utilizing three or more instruments, or a single instrument.

Although vitreous surgery is discussed as an example of a surgical procedure that may benefit from the described embodiments, the advantages of the surgical devices and systems described herein may benefit other surgical procedures as well.

EXAMPLE EMBODIMENTS

Embodiment 1: A surgical instrument for performing an ophthalmic surgical procedure, comprising: a handpiece; and a probe disposed through an opening in a distal end of the handpiece and configured to be inserted into an intraocular space of an eye, the probe comprising: an infusion portion having a first diameter, the infusion portion comprising: a port for directing fluid into a surgical site within the intraocular space; and a channel fluidly coupled to the port for delivering the fluid to the port; and a treatment portion distal to the infusion portion and having a second diameter smaller than the first diameter, the treatment portion comprising: a device for treating a tissue at a surgical site.

Embodiment 2: The surgical instrument of Embodiment 1, wherein the device is a mechanical tool for manipulating the tissue at the surgical site.

Embodiment 3: The surgical instrument of Embodiment 2, wherein the device comprises scissors.

Embodiment 4: The surgical instrument of Embodiment 2, wherein the device comprises forceps.

Embodiment 5: The surgical instrument of Embodiment 1, wherein a distal end of the treatment portion comprises a beveled end face.

Embodiment 6: A system for performing an ophthalmic surgical procedure, comprising: an endoillumination instrument; and a treatment instrument for treating a tissue in an intraocular space of an eye, comprising: a handpiece; and a probe disposed through an opening in a distal end of the handpiece and configured to be inserted into the intraocular space of the eye, the probe comprising: an infusion portion having a first diameter, the infusion portion comprising: a port for directing fluid into a surgical site within the intraocular space; and a channel fluidly coupled to the port for delivering the fluid to the port; and a treatment portion distal to the infusion portion and having a second diameter smaller than the first diameter, the treatment portion comprising: a device for treating a tissue at a surgical site, wherein at least one of the endoillumination instrument and the treatment instrument are configured to be manipulated by a surgeon to control a position of an eye during the ophthalmic surgical procedure.

Embodiment 7: The surgical instrument of Embodiment 6, wherein the infusion portion has a diameter of 23 gauge and the treatment portion has a diameter of 25 gauge.

Embodiment 8: The surgical instrument of Embodiment 6, wherein the infusion portion has a diameter of 25 gauge and the treatment portion has a diameter of 27 gauge.

Embodiment 9: The surgical instrument of Embodiment 6, wherein the infusion portion has a diameter of 27 gauge and the treatment portion has a diameter of 29 gauge Embodiment 10: The surgical instrument of Embodiment 6, wherein the infusion portion comprises 50% to about 60% and about 90% of a length of the probe.

Embodiment 11: The surgical instrument of Embodiment 6, wherein the infusion portion comprises 50% to about 75% of the length of the probe.

Embodiment 12: The surgical instrument of Embodiment 6, wherein the device is a mechanical tool for manipulating the tissue at the surgical site.

Embodiment 13: The surgical instrument of Embodiment 12, wherein the device comprises scissors.

Embodiment 14: The surgical instrument of Embodiment 12, wherein the device comprises forceps.

Embodiment 15: The surgical instrument of Embodiment 6, wherein a distal end of the treatment portion comprises a beveled end face.

The above-disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A surgical instrument for performing an ophthalmic surgical procedure, comprising:

a handpiece; and a probe at a distal end of the handpiece configured to be inserted into an intraocular space of an eye, the probe comprising:

an infusion portion having a first diameter, the infusion portion comprising:

a port for directing fluid into a surgical site within the intraocular space; and a channel fluidly coupled to the port for delivering the fluid to the port; and a treatment portion distal to the infusion portion and having a second diameter smaller than the first diameter, the treatment portion comprising:

a device for treating a tissue at a surgical site, comprising:

a sealed laser probe having a tube with a window press fit into a distal end of the tube;

one or more optical fibers extending down a length of an interior of the sealed laser probe tube to deliver laser light and illumination light through the window and illumination light through a distal side wall of the sealed laser probe tube;

wherein the sealed laser probe tube comprises masking along a majority of a length of the laser probe tube except the distal side wall which comprises at least a ¼ of a length of the laser probe tube extending from the distal end of the sealed laser probe tube.

2. The surgical instrument of claim 1, wherein the device is a non-aspirating laser vitrectomy device.

3. The surgical instrument of claim 1, wherein the device is an elongated laser-propagating member for performing endophotocoaguation or laser ablation.

4. The surgical instrument of claim 1, wherein the infusion portion has a diameter of 23 gauge and the treatment portion has a diameter of 25 gauge.

5. The surgical instrument of claim 1, wherein the infusion portion has a diameter of 25 gauge and the treatment portion has a diameter of 27 gauge.

6. The surgical instrument of claim 1, wherein the infusion portion has a diameter of 27 gauge and the treatment portion has a diameter of 29 gauge.

7. The surgical instrument of claim 1, wherein a length of the infusion portion is about 50% to about 90% of a length of the probe.

8. The surgical instrument of claim 1, wherein a length of the infusion portion is about 50% to about 75% of the length of the probe.

9. A system for performing an ophthalmic surgical procedure, comprising:

an endoillumination instrument; and a treatment instrument for treating a tissue in an intraocular space of an eye, comprising:

a handpiece; and a probe at a distal end of the handpiece configured to be inserted into the intraocular space of the eye, the probe comprising:

an infusion portion having a first diameter, the infusion portion comprising:

a port for directing fluid into a surgical site within the intraocular space; and a channel fluidly coupled to the port for delivering the fluid to the port; and a treatment portion distal to the infusion portion and having a second diameter smaller than the first diameter, the treatment portion comprising:

a device for treating a tissue at a surgical site, wherein at least one of the endoillumination instrument and the treatment instrument are configured to be manipulated by a surgeon to control a position of an eye during the ophthalmic surgical procedure;

wherein the device comprises:

a sealed laser probe having a tube with a window press fit into a distal end of the tube;

one or more optical fibers extending down a length of an interior of the sealed laser probe tube to deliver laser light and illumination light through the window and illumination light through a distal side wall of the sealed laser probe tube;

wherein the sealed laser probe tube comprises masking along a majority of a length of the laser probe tube except the distal side wall which comprises at least a ¼ of a length of the laser probe tube extending from the distal end of the sealed laser probe tube.

10. The system of claim 9, wherein the device is a non-aspirating laser vitrectomy device.

11. The system of claim 9, wherein the device is an elongated laser-propagating member for performing endo-photocoaguation or laser ablation.

* * * * *